(12) United States Patent
Lesser

(10) Patent No.: US 7,801,740 B1
(45) Date of Patent: Sep. 21, 2010

(54) SOFTWARE DEVICE TO FACILITATE CREATION OF MEDICAL RECORDS, MEDICAL LETTERS, AND MEDICAL INFORMATION FOR BILLING PURPOSES

(76) Inventor: Ronald Peter Lesser, 709 Stevenson La., Baltimore, MD (US) 21286-7905

( * ) Notice: Subject to any disclaimer, the term of this patent is extended or adjusted under 35 U.S.C. 154(b) by 0 days.

(21) Appl. No.: 09/157,998

(22) Filed: Sep. 22, 1998

(51) Int. Cl.
*G06Q 10/00* (2006.01)
(52) U.S. Cl. .............................. 705/2; 705/3; 600/300
(58) Field of Classification Search ................. 705/2–3, 705/4
See application file for complete search history.

(56) References Cited

U.S. PATENT DOCUMENTS

| | | | |
|---|---|---|---|
| 4,130,881 A | 12/1978 | Haessler | |
| 5,001,630 A | 3/1991 | Wiltfong | |
| 5,077,666 A * | 12/1991 | Brimm et al. | 705/4 |
| 5,325,293 A * | 6/1994 | Dorne | 705/2 |
| 5,483,443 A | 1/1996 | Milstein | |
| 5,612,869 A * | 3/1997 | Letzt | 705/3 |
| 5,704,371 A * | 1/1998 | Shepard | 128/897 |
| 5,732,221 A | 3/1998 | Feldon | |
| 5,781,891 A | 7/1998 | Dvorak | |
| 5,794,208 A | 8/1998 | Goltra | |
| 5,802,495 A | 9/1998 | Goltra | |
| 5,823,948 A | 10/1998 | Ross, Jr. et al. | |
| 5,832,450 A | 11/1998 | Myers et al. | |
| 5,845,253 A | 12/1998 | Rensimer et al. | |

(Continued)

OTHER PUBLICATIONS

Groves;"Dynamic Computer System for Clinical Laboratory" American Journal Of Medical Technology v44 n6 p. 575-581; Dialog, File: 6, Accession No. 0738190, Jun. 1978.*

(Continued)

*Primary Examiner*—Robert W Morgan
(74) *Attorney, Agent, or Firm*—J Mark Holland & Assoc.

(57) ABSTRACT

A method is described which simplifies, automates and organizes the creation of notes and correspondence and also, by performing the calculations needed to determine the appropriate billing codes, provides documentation for billing purposes. It also assists the health care worker in determining the proper billing code. An embodiment of this to facilitate the creation of documents in the setting of patient care is described. The use of this for medical records is particularly of importance because of recent government (Heath Care and Finance Administration, or HCFA) regulations. The embodiment also allows one to enter information into a patient database at the same time that one is entering clinical information for the purposes of clinical care documentation. The database could be for clinical care, quality assurance, or research purposes. The embodiment describes how this can be achieved at the time that a service is delivered, for example when a health care worker sees a patient. Because the data is entered at the time of service, time is saved, and the information is more accurate. Although the embodiment describes a use in health care, this could be used in any industry. The invention allows one to enter information about patients using a combination of checklists, menus, and fill in the blank formats. The invention could use any handheld or desktop computer. Data entry also could be accomplished using scanner-enabled paper forms similar to those used by questionnaires or by tests such as the Scholastic Aptitude Test, with the user filling in the appropriate circles or other spaces to indicate the answer.

37 Claims, 18 Drawing Sheets

Elements of a Medical History and Physical

American Medical Association
Health Care Financing Administration

- History
  - History of Present Illness
  - Review of Systems
  - Past History
    Family History
    Social History

- Physical Examination
  - 7 body areas / 12 organ systems

- Complexity / Medical Decision Making
  - Number of Options
    Risk
  - Data Amount/Complexity

U.S. PATENT DOCUMENTS

| | | | | |
|---|---|---|---|---|
| 5,893,098 A | * | 4/1999 | Peters et al. | 707/10 |
| 5,924,074 A | * | 7/1999 | Evans | 705/3 |
| 5,964,700 A | * | 10/1999 | Tallman et al. | 600/300 |
| 5,970,463 A | * | 10/1999 | Cave et al. | 705/3 |
| 6,026,363 A | * | 2/2000 | Shepard | 705/3 |
| 6,151,581 A | * | 11/2000 | Kraftson et al. | 705/3 |
| 6,223,164 B1 | * | 4/2001 | Seare et al. | 705/2 |

OTHER PUBLICATIONS

"Raynbow Technology"; Computer Reseller News; Dialog, File: 160, Accession No. 01885033, Mar. 1988.*

Joseph et al. "Defining Medical Record and Financial Department Relationship"; Healthcare Financial Management v39n7 pp. 70-74; Dialog, File: 15, Accession No. 00287658, Jul. 1985.*

Steven et al; "The computer-based medical record: current status"; Journal of Family Practice, v35, n5, p. 556(10); Dialog, File:149, Accession No. 01374326, Nov. 1992.*

"Technology Analysis—Wireless LANs Get Connected—"; Information Week, p. 78; Dialog, File: 16, Accession No. 04498233, Aug. 1996.*

IaTrosoft Corp.—ePatient http://www.iatrosoft.com/.
Emergence http://www.opendoor.com/badcat/emergence.html.
Azron Inc.—Azron EMR http://www.azron.com.
Careis#1 Merritt http://www.careis1.com.
Clinicare Corporation—CMR http://www.CLINICARE.com/.
Docs, Inc SOAPware http://www.docs.com.
JMJ Technologies, Inc.—EncounterPRO http://www.jmjtech.com.
Medicalogic Inc. Logician http://www.medicalogic.com.
Medicware, Inc.—medicwareEMR http://www.medicware.com.
Oceania, Inc—Wave http://www.oceania.com.
Patient Medical Records, Inc. S-O-A-P http://www.pmrinc.com.
Physix, Inc.—PocketChart http://www.physix.com.
Health Care Information Systems—PointCare http://www.hcisinc.com.
Power Med Corp.—PowerMed EMR http://www.powermed.com.
Sirius Technologies Medmaster http://www.siriustech.com.
Synapse Software Rounder http://www.synapsesoft.com.
Austin Physician Productivity LLC. Stat E&M Coder http://www.statcoder.com.
NNK Research Group—Zap Coder http://www.nnk.com/hcfaem/.
Medical Communication Systems Mobile Med Data http://www.medcomsys.com/palmpilot.htm.
Maulin Shah—PatientKeeper http://www.patientkeeper.com.
IDX Systems Corp. IDXtend http://www.idx.com/.
Pocket MD—PocketMD http://www.PocketMD.com.
Penchart Corporation—Penchart http://www.penchart.com.
E-Chart e-chart http://www.e-chart.com.
Turbo-Doc Medical Records Systems, Inc.—Turbo-Doc http://www.turbodoc.com.
American Medical Software Computerized Patient Record System http://www.americanmedical.com.
Rostov Software Ind., Ltd., Clicks Medical information System http://www.roshtov.com/.
Infor*Med Corporation—PraxisEMR http://www.infor-med.com/websiteIII/door!.htm.
Stone Enterprises Medical Software, Inc Ent Medical Dictator http://www.stoneent.com.
Shared Medical Systems—Novius Encounter http://www.smed.com/.
McKessonHBOC Pathways SMR http://www.hboc.com.
American Medical Software—The Electronic Medical Chart http://www.emcmedicalchart.com/.

Bergeron BP and Greenes RA. Intelligent Visual Input: A Graphical Method for Rapid Entry of Patient-Specific Data. 11th Symposium on Computer Applications In Medical Care. Computer Society Press. 1987. pp. 281-286.

Hammond JE et al. The Physician's Workstation: an Example of End User Integration of Information Systems. 16th Symposium on Computer Applications In Medical Care. AMIA, 1992. pp. 970-972.

Lussier et al. PureMD: a Computerized Patient Record Software for Direct Data Entry by Physicians Using a Keyboard-free Pen-Based Portable Computer. 16th Symposium on Computer Applications In Medical Care. AMIA, 1993. pp. 261-263.

Campbell et al. A Computer-based Tool for Generation of Progress Notes. 17th Symposium on Computer Applications In Medical Care. AMIA, 1994. pp. 284-288.

Poon AD and Fagai LM. The Design and Evaluation of a Pen-Based Computer System for Structured Data Entry. J Amer Med Informatics Assn, 1994. 1(suppl 1):pp. 447-451.

Kahane IS. Getting the Data In: Three Year Experience With a Pediatric Electronic Medical Record System. J Amer Med Informatics Assn, 1994. 1(suppl 1):pp. 457-460.

Wenner AR et al. Instant Medical History. J Amer Med Informatics Assn, 1994. 1(suppl 1): p. 1036.

Defriece RJ. Design Considerations for Intelligent Data Entry: Development of MedIO. J Amer Med Informatics Assn, 1995. 2 (suppl 1): pp. 91-95.

Bressler NM, Cain RV, and Steigerwald DG. An Intelligent Pen-Based Ophthalmologic Patient Record. J Amer Med Informatics Assn, 1995. 2 (suppl 1): p. 1009.

Kirby J and Rector AL. The PEN&PAD Data Entry System: From prototype to practical system. J Amer Med Informatics Assn, 1996. 3 (suppl 1):pp. 709-713.

Grant AM et al. Evaluation of the Newton Pen-Pad as a Tool for Collecting Clinical Research Data at the Bed-side..J Amer Med Informatics Assn, 1996. 3 (suppl 1):738-41.

Rosenthal DF et al.. A Voice-enabled, Structured Medical Reporting System. J Amer Med Inform Assoc. 1997. 4:436-441.

Van Mulligen EM. et al. Clinical Data Entry. J Amer Med Informatics Assn, 1998. 5(suppl 1):81-85.

Melles RB et al. . User Interface Preferences in a Point-of-care Data System. J Amer Med Inform Assn. pp. 261-263.

Folz-Murphy. Physician Use of an Ambulatory Medical Record System: Matching Form and Function. 17th Symposium on Computer Applications in Medical Care. J Amer Med Inform Assn, 1998. pp. 260-264.

* cited by examiner

Elements of a Medical History and Physical

American Medical Association
Health Care Financing Administration

- History
  - History of Present Illness
  - Review of Systems
  - Past History
    Family History
    Social History

- Physical Examination
  - 7 body areas / 12 organ systems

- Complexity / Medical Decision Making
  - Number of Options
    Risk
  - Data Amount/Complexity

Figure 1a.

Elements of the History

- Chief Complaint
- History of Present Illness
  - location, quality, severity, duration, timing, context, modifying factors, associated signs and symptoms
- Scoring
  - brief     1-3 elements
  - extended     4 elements, current
                        3 elements, chronic inactive

Figure 1b.

Review of Systems

- Systems
  - Constitutional Eyes
  - Ears, Nose, Mouth, Throat
  - CardiovascularRespiratory
  - Gastrointestinal
  - Genitourinary
  - Musculoskeletal
  - Integumentary
  - Neurologic
  - Psychiatric
  - Endocrine
  - Hematologic \ lymphatic
  - Allergic \ Immunologic

- Scoring
  - problem pertinent      system related to problem
  - extended               2-9 systems including system related to problem
  - complete               10 system

Figure 1c.

Past, Family, Social History

- Scoring
  - pertinent    one item
  - complete    two of three areas
    - outpatient, established
    - domiciliary, established
    - home care, established
    - emergency department
  - complete    three of three areas
    - outpatient, new
    - inpatient, new
    - domiciliary, new
    - home care, new
    - nursing facility, comprehensive
    - hospital observation
    - consults

Figure 1d.

History - scoring all elements must be met

| History of Present Illness (HPI) | Review of Systems (ROS) | Past, Family and/or Social History (PFSH) | Type of History |
|---|---|---|---|
| Brief | N/A | N/A | Problem Focused |
| Brief | Problem Pertinent | N/A | Expanded Problem Focused |
| Extended | Extended | Pertinent | Detailed |
| Extended | Complete | Complete | Comprehensive |

Figure 1e.

Examination

- Systems
  - General multi-system
  - Specialty

| | |
    |---|---|
    | cardiovascular | Ears nose mouth throat |
    | eyes | genitourinary (male, female) |
    | musculoskeletal | neurological |
    | psychiatric | respiratory |
    | skin | |
    | hematologic/lymphatic/immunologic | |

- Scoring

| | |
  |---|---|
  | – problem focused | affected area/system<br>1-5 bulleted elements |
  | – expanded problem focused | affected system plus other symptomatic or related body areas<br>six bulleted elements |
  | – detailed | 12 bulleted elements<br>(9 elements - eye, psychiatric) |
  | – comprehensive | all bulleted elements<br>all shaded elements, one unshaded element |

Figure 1f.

Coding table
System/Body Area vs. Specialty

|  |  | Specialty 1 | Specialty 2 | Specialty 3 | Specialty 4 |
|---|---|---|---|---|---|
| System / Body Area 1 | Element 1 | 0111 | 0101 | 1000 | 1000 |
| System / Body Area 1 | Element 2 | 0111 | 1000 | 0111 | 0101 |
| System / Body Area 1 | Element 3 | 1000 | 0111 | 0111 | 0111 |
| System / Body Area 1 | Element 4 | 0011 | 0101 | 0101 | 1000 |
| System / Body Area 2 | Element 5 | 0100 | 0111 | 0100 | 0111 |
| System / Body Area 2 | Element 6 | 0010 | 0100 | 1000 | 0111 |
| System / Body Area 2 | Element 7 | 0011 | 0100 | 0111 | 0101 |
| System / Body Area 2 | Element 8 | 1000 | 0100 | 0100 | 0101 |

Figure 1f1.

Neurological Examination

| System/Body Area | Elements of Examination |
|---|---|
| Constitutional | • Measurement of any three of the following seven vital signs: 1) sitting or standing blood pressure, 2) supine blood pressure, 3) pulse rate and regularity, 4) respiration, 5) temperature, 6) height, 7) weight (May be measured and recorded by ancillary staff)<br><br>• General appearance of patient (eg, development, nutrition, body habitus, deformities, attention to grooming) |
| Head and Face | |
| Eyes | Ophthalmoscopic examination of optic discs (eg, size, C/D ratio, appearance) and posterior segments (eg, vessel changes, exudates, hemorrhages) |
| Ears, Nose, Mouth and Throat | |
| Neck | |
| Respiratory | |
| Cardiovascular | Examination of carotid arteries (eg, pulse amplitude, bruits)<br><br>• Auscultation of heart with notation of abnormal sounds and murmurs<br><br>• Examination of peripheral vascular system by observation (eg, swelling, varicosities) and palpation (eg, pulses, temperature, edema, tenderness) |
| Chest (Breasts) | |
| Gastrointestinal (Abdomen) | |
| Genitourinary | |
| Lymphatic | |

Figure 1g.

| | |
|---|---|
| Musculoskeletal | • Examination of gait and station<br><br>Assessment of motor function including:<br><br>· Muscle strength in upper and lower extremities<br><br>· Muscle tone in upper and lower extremities (eg, flaccid, cog wheel, spastic) with notation of any atrophy or abnormal movements (eg, fasciculation, tardive dyskinesia) |
| Extremities | [See musculoskeletal] |
| Skin | |
| Neurological | Evaluation of higher integrative functions including:<br><br>· Orientation to time, place and person<br><br>· Recent and remote memory<br><br>· Attention span and concentration<br><br>· Language (eg, naming objects, repeating phrases, spontaneous speech)<br><br>· Fund of knowledge (eg, awareness of current events, past history, vocabulary)<br><br>Test the following cranial nerves:<br><br>· 2nd cranial nerve (eg, visual acuity, visual fields, fundi)<br>· 3rd, 4th and 6th cranial nerves (eg, pupils, eye movements)<br>· 5th cranial nerve (eg, facial sensation, corneal reflexes)<br>· 7th cranial nerve (eg, facial symmetry, strength)<br>· 8th cranial nerve (eg, hearing with tuning fork, whispered voice and/or finger rub)<br>· 9th cranial nerve (eg, spontaneous or reflex palate movement)<br>· 11th cranial nerve (eg, shoulder shrug strength)<br>· 12th cranial nerve (eg, tongue protrusion)<br><br>• Examination of sensation (eg, by touch, pin, vibration, proprioception)<br><br>• Examination of deep tendon reflexes in upper and lower extremities with notation of pathological reflexes (eg, Babinski)<br><br>• Test coordination (eg, finger/nose, heel/knee/shin, rapid alternating movements in the upper and lower extremities, evaluation of fine motor coordination in young children) |
| Psychiatric | |

Figure 1h.

Complexity of Medical Decision Making

| # of options | Amount, complexity of data | Risk of complications morbidity mortality | Type of decision making |
|---|---|---|---|
| Minimal | Minimal or none | Minimal | Straight-forward |
| Limited | Limited | Low | Low Complexity |
| Multiple | Moderate | Moderate | Moderate Complexity |
| Extensive | Extensive | High | High Complexity |

Figure 1i.

TABLE OF RISK

| Level of Risk | Presenting Problem(s) | Diagnostic Procedure(s) Ordered | Management Options Selected |
|---|---|---|---|
| *Minimal* | • One self-limited or minor problem, eg, cold, insect bite, tinea corporis | • Laboratory tests requiring venipuncture<br>• Chest x-rays<br>• EKG/EEG<br>• Urinalysis<br>• Ultrasound, eg, echocardiography<br>• KOH prep | • Rest<br>• Gargles<br>• Elastic bandages<br>• Superficial dressings |
| *Low* | • Two or more self-limited or minor problems<br>• One stable chronic illness, eg, well controlled hypertension, non-insulin dependent diabetes, cataract, BPH<br>• Acute uncomplicated illness or injury, eg, cystitis, allergic rhinitis, simple sprain | • Physiologic tests not under stress, eg, pulmonary function tests<br>• Non-cardiovascular imaging studies with contrast, eg, barium enema<br>• Superficial needle biopsies<br>• Clinical laboratory tests requiring arterial puncture<br>• Skin biopsies | • Over-the-counter drugs<br>• Minor surgery with no identified risk factors<br>• Physical therapy<br>• Occupational therapy<br>• IV fluids without additives |
| *Moderate* | • One or more chronic illnesses with mild exacerbation, progression, or side effects of treatment<br>• Two or more stable chronic illnesses<br>• Undiagnosed new problem with uncertain prognosis, eg, lump in breast<br>• Acute illness with systemic symptoms, eg, pyelonephritis, pneumonitis, colitis<br>• Acute complicated injury, eg, head injury with brief loss of consciousness | • Physiologic tests under stress, eg, cardiac stress test, fetal contraction stress test<br>• Diagnostic endoscopies with no identified risk factors<br>• Deep needle or incisional biopsy<br>• Cardiovascular imaging studies with contrast and no identified risk factors, eg, arteriogram, cardiac catheterization<br>• Obtain fluid from body cavity, eg lumbar puncture, thoracentesis, culdocentesis | • Minor surgery with identified risk factors<br>• Elective major surgery (open, percutaneous or endoscopic) with no identified risk factors<br>• Prescription drug management<br>• Therapeutic nuclear medicine<br>• IV fluids with additives<br>• Closed treatment of fracture or dislocation without manipulation |
| *High* | • One or more chronic illnesses with severe exacerbation, progression, or side effects of treatment<br>• Acute or chronic illnesses or injuries that pose a threat to life or bodily function, eg, multiple trauma, acute MI, pulmonary embolus, severe respiratory distress, progressive severe rheumatoid arthritis, psychiatric illness with potential threat to self or others, peritonitis, acute renal failure<br>• An abrupt change in neurologic status, eg, seizure, TIA, weakness, sensory loss | • Cardiovascular imaging studies with contrast with identified risk factors<br>• Cardiac electrophysiological tests<br>• Diagnostic Endoscopies with identified risk factors<br>• Discography | • Elective major surgery (open, percutaneous or endoscopic) with identified risk factors<br>• Emergency major surgery (open, percutaneous or endoscopic)<br>• Parenteral controlled substances<br>• Drug therapy requiring intensive monitoring for toxicity<br>• Decision not to resuscitate or to de-escalate care because of poor prognosis |

Figure 1j.

| Initial hosp | | 9922X | 331 | 443 | 444 | | |
|---|---|---|---|---|---|---|---|
| p. 28 | "3/3 | | 1 | 2 | 3 | | |
| | | | 30 | 50 | 70 | | |
| A1B1C1 | A1B1C2 | A1B1C3 | A1B1C4 | A1B2C1 | A1B2C2 | A1B2C3 | A1B2C4 |
| n | n | n | n | n | n | n | n |
| A1B3C1 | A1B3C2 | A1B3C3 | A1B3C4 | A1B4C1 | A1B4C2 | A1B4C3 | A1B4C4 |
| n | n | n | n | n | n | n | n |
| A2B1C1 | A2B1C2 | A2B1C3 | A2B1C4 | A2B2C1 | A2B2C2 | A2B2C3 | A2B2C4 |
| n | n | n | n | n | n | n | n |
| A2B3C1 | A2B3C2 | A2B3C3 | A2B3C4 | A2B4C1 | A2B4C2 | A2B4C3 | A2B4C4 |
| n | n | n | n | n | n | n | n |
| A3B1C1 | A3B1C2 | A3B1C3 | A3B1C4 | A3B2C1 | A3B2C2 | A3B2C3 | A3B2C4 |
| n | n | n | n | n | n | n | n |
| A3B3C1 | A3B3C2 | A3B3C3 | A3B3C4 | A3B4C1 | A3B4C2 | A3B4C3 | A3B4C4 |
| 1 | 1 | 1 | 1 | 1 | 1 | 1 | 1 |
| A4B1C1 | A4B1C2 | A4B1C3 | A4B1C4 | A4B2C1 | A4B2C2 | A4B2C3 | A4B2C4 |
| n | n | n | n | n | n | n | n |
| A4B3C1 | A4B3C2 | A4B3C3 | A4B3C4 | A4B4C1 | A4B4C2 | A4B4C3 | A4B4C4 |
| 1 | 1 | 1 | 1 | 1 | 1 | 2 | 3 |

Figure 4c.

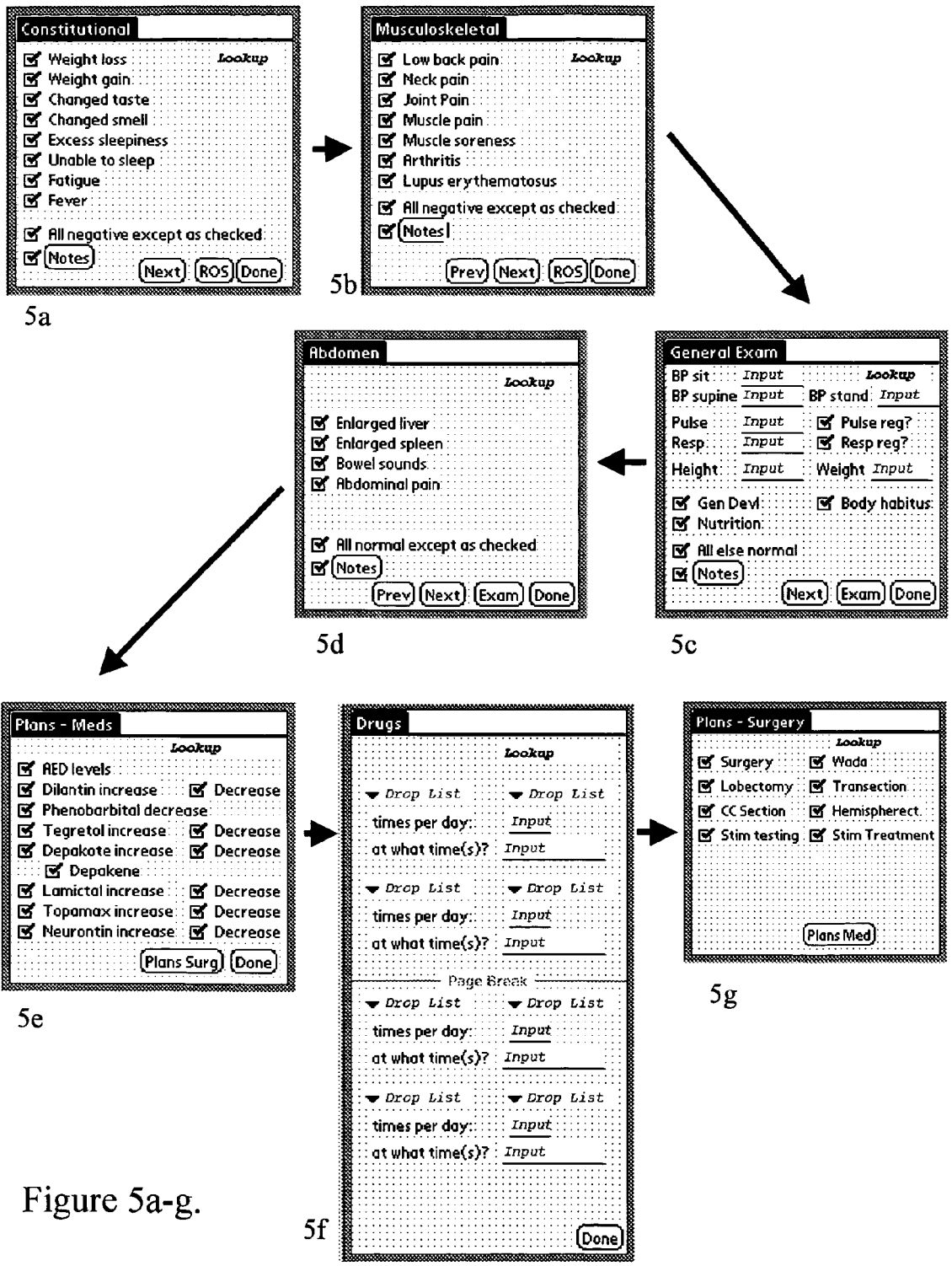
Figure 5a-g.

Figure 5h-i.

SOFTWARE DEVICE TO FACILITATE CREATION OF MEDICAL RECORDS, MEDICAL LETTERS, AND MEDICAL INFORMATION FOR BILLING PURPOSES

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

There has been considerable concern over the past few years regarding the expansion in the amount of medical information available in general as well as with respect to individual patients. At the same time as there are increasing pressures on health care workers to document as fully as possible, there are pressures to provide care as efficiently as possible. In general, care is given to a patient and the health care worker afterwards writes a note in a chart, or dictates a note, describing the activity. This information is "inscribed" in a relatively free form fashion. While this is useful and important as a way of preserving certain kinds of clinical information, it impedes medical care at other times because of the lack of standardization of terms and concepts. Finally, when notes are hand written they are often difficult for others to read.

Increased documentation is being requested by third party organizations. The lack of structure to medical notes often results in an increase in accounts receivable for care givers (that is, an increase in the backlog of bills which haven't been paid). This is because questions are asked about a rendered service, the chart needs to be found, the appropriate information extracted, and information sent back to the payer. Individual practitioners, academic institutions, pharmaceutical companies, and others in the health care industry have an interest not only in gathering patient related information but also in assessing the quality of the care, and in developing new methods of care. The Health Care Financing Administration (HCFA) a branch of the United States Department of Health and Human Services, in keeping with this trend, has published, in conjunction with the American Medical Association, a list of detailed requirements for billing at various levels.

Health care providers would like to document the care they give as efficiently and accurately as possible. However, today a health care worker typically must indicate the results of the encounter, given current methods, after the patient is seen. This increases the burden on the individual health care provider. It increases the cost of gathering the data, regardless of whether information is entered by the original provider or by someone else. Because memory is faulty, even recent memory, it increases the likelihood of errors (both mis-statements and omissions).

There has been a general increase in automation over the past several decades as a way of meeting some of these needs. For medical care, a number of companies have developed electronic medical information repositories. On the simplest levels, these repositories, often called electronic medical records or electronic patient records, include clinical notes, discharge summaries, and operative notes, all of these the result of dictation. Laboratory reports also are typically included. The advantage of these repositories is that notes are in a legible form since they are dictated by the practitioner and then "typed." Moreover, they are stored in a common repository so that it becomes easier to find all the information, or at least much of the information, on a given patient. The disadvantage is that the information in many implementations is free form. Thus specific items of information are harder to find. This in turn means that the goals of clinical studies or clinical research are not met. If payers request specific kinds of information the information must be sought by a close reading of the text with automation relatively difficult. If information is to be obtained, diagnoses made, and care administered according to a protocol, there is no way of ensuring that this has occurred in the case of an individual patient without actually reading the record. Finally there are no ways of enhancing or facilitating data entry. Even though dictation is faster than writing, it usually is done at a time after the patient is seen and can be quite time consuming. To meet these needs, a number of companies have introduced systems for entering medical information through the use of organized menus. The user chooses from a list or lists the items pertinent to the visit. The computer program then develops a chart note based upon the choices entered. The disadvantage of this has been a lack of physician acceptance: many feel constrained by the programs, feel that they are more time consuming than dictation, and that the available choices do not reflect important aspects of the patient encounter.

PRIOR ART

Electronic medical record development has been the subject of both commercial and academic interest for decades, but no current method has been entirely successful. Most require the health care worker to be at a personal computer, or computer terminal. There are a large number of such programs. (Logician form MedicaLogic and HealthMatics Series 4 from HealthMatics are two examples). The disadvantage of these is that much of medical care is mobile: the doctor is walking around the hospital, the nurse is going from patient room to patient room, the home health care worker is going from home to home. Although one could carry a laptop computer, these are relatively large. Consider what the health care practitioners do when seeing or caring for patients. They need often to carry several diagnostic tools, medications, pieces of equipment, etc. They need to have both hands free to diagnose or care for the patient. A laptop might need to be opened up and closed as each patient is seen, even if it can be turned on instantly. There needs to be a place to put the laptop when it is used, and often there are no available surfaces. A large stationary computer or computer terminal (if there is space for one) would require a more elaborate and lengthy sign-on process each time to assure security of patient information, and to insure that the right person is accessing the computer or computer network. Also, in many patient settings, a large computer terminal and keyboard might be considered intrusive by the patient, and might actually impede the development of an appropriate relationship with the patient. Conversely, and perhaps perversely, the patient might find the device intriguing and interesting, and would want "to take a look"—a look which would take time away from considering the patient's problems and which would make the overall use of the practitioner's time less efficient. To address the size problem, several companies have developed methods of using portable devices for entering data on patients. One example would be Pocket Chart from Physix, Inc. Another is Mobile MedData, made by Medical Communications Systems.

Feldon and Agrawal have described an "Electronic Documentation System for Generating Written Reports" (U.S. Pat. No. 5,732,221). The preferred embodiment of this invention uses a GridPad, a larger pen-based system. This includes a method for defining menu items and then a method for displaying these items in menus. It defines items such as titles, nouns, pronouns, and adjectives from which the user selects to generate a report. Based on the selections by the user, a written report is generated.

Haessler, Elshtain, and Holland have described a "System and Technique for Automated Medical History Taking" (U.S. Pat. No. 4,130,881). This uses a branching method to assist in automatically taking a history from a patient. When particular answers are given, the system then asks pertinent related questions. The patient does this, so that the answers later are available to the physician. Such a system could gather initial pertinent positive and negative information for the health care provider.

Similarly, Goltra has described a method for "Creating and Using Protocols to Create and Review a Patient Chart" (U.S. Pat. No. 5,794,208) and "Phrasing Structure for the Narrative Display of Findings" (U.S. Pat. No. 5,802,495). The first of these discloses a method for developing disease or symptom-specific protocols for examining a patient. This is accomplished by submitting features of the patient's history and examination (for example) to a database. Based on the findings, the database develops a disease specific examination protocol. This protocol could then be utilized on a computer to indicate the results of examining the patient. The second discloses a method, based on the health care professional's findings, for generating the text of a narrative report of the examination.

Dorne has disclosed "System and Method for Correlating Medical Procedures and Medical Billing Codes" (U.S. Pat. No. 5,325,293). This is a method for collecting all of the aspects of a radiological examination so that the total billing code can be calculated. ("Procedure" is a term used in health care to denote radiological examinations, surgical operations, and similar methods of diagnosis or treatment.) Milstein, Maguire, and Meier have disclosed "Method for Computing Current Procedural Terminology Codes from Physician Generated Documentation" (U.S. Pat. No. 5,483,443). This method displays "a set of queries to the medical professional" and determines the appropriate coding level based on the results of these queries.

SUMMARY OF THE INVENTION

While all of these methods include ways of documenting medical care, they all have in common a need to navigate through several layers of menus and submenus. Navigation through multiple menu layers is time consuming and can take the users attention away from caring for the patient. Furthermore, not everyone feels comfortable using computers, even small computers, and in navigating menus. Finally, the best time to be certain that a particular patient encounter meets HCFA guidelines for a particular level of service is at the time of the encounter, not later. However, the reason for the patient encounter is to take care of the patient, not to generate the bill. If at all possible, billing should not distract from patient care. The present invention integrates billing documentation into the history and physical documentation process. It allows written reports and also allows for reports to be generated in more than one format. For example, reports to patients and to professional users could differ from one another, as might be appropriate for the particular kind of correspondence. The invention described here also allows for generation of information for multiple needs, including correspondence, patient care, quality assurance, and research.

The method described here uses a small and inconspicuous portable device or could use paper, but also could use desktop computers if preferred by the practitioner, or if more appropriate for a given situation. The format is a checklist format, organized in the order in which the particular health care worker is accustomed to acquire the information. The health care worker can modify the order of data entry. Patients have long experience with physicians taking notes on paper (using either blank pieces of paper or forms) so that this is a "cosmetically" more acceptable data entry method. The goal is to follow this way of gathering information. As noted, there are commercial products that use hand held devices. Some require text entry into the device, and this is cumbersome in the setting of clinical care. At other times, devices use more "formatted" data entry, but the layers of menus and submenus can be confusing for some health care workers, and the time to navigate the menus can be substantial. The software described here allows both form driven and free text entry (including entry by dictation), and allows form driven data entry to be integrated with free text at a later point in time. It avoids the use of layers of menus. It allows the user to decide the order of data entry when the patient is seen. The device allows not only free text entry into the program but also free text entry by means of writing or dictation. No menu system will ever allow one to capture all of the important nuances of the problems of an individual patient. The system allows the free text and menu driven information to be integrated afterwards. Finally, the present invention differs from its predecessors in that it explicitly combines the HCFA regulations into the broader set of all the history, physical examination, and patient care items that might be part of a given patient evaluation. This creates a complete structure of the patient history and physical examination. It does this in a way that allows easy "maintenance" so that, as the rules change, the implementation within the program can be modified easily.

Rather than developing an overly complicated format that includes increasingly more possibilities, this method tries to provide a simple format, to which more complicated information can be easily added. (See below and illustrations) Finally this device allows output that can provide clinical research, quality control, or patient care data base information, clinical notes, correspondence, and billing information at one time and without further intervention.

The device is a simple system that allows the practitioner to encode a high percentage, perhaps three-quarters or more, of the information from a patient encounter. The system uses a combination of check boxes, selections from forms, and the like. The system avoids the use of multiple layers of menus on data selection pages. Rather, it allows the practitioner to move in a relatively linear fashion through the history and examination process. The idea of this software is that, for many practitioners, what is done in the case of a particular encounter is fairly standard for the problem that generated the encounter. This is true both for generalists and specialists. The system includes questions that need to be asked in order to review the general medical state of the individual and includes items required under the HCFA documentation scheme. All information is entered into a database. The software allows development of data entry screens that relate to the data base tables. The software allows the portable device to exchange information with any standard database Because no format can ever be expected to reflect the all the nuances of an individual patient encounter, the device includes a method that allows the practitioner to indicate that dictation, or "written" or "typed" notes will be added. (In the context of this submission, dictation is meant to imply voice entry into either a desktop or portable recorder or into a computer with either later transcription by a human typist or by means of speech recognition. "Written" is meant to imply writing with either character recognition or bit map capture subsequently. "Typing" any method of keying in information that later will be or could be incorporated into a record.) This is provided throughout the entry record, so that each addendum is keyed to a specific part of the history, physical examination, or assessment and management process. The idea is that the practitioner can note the results of the encounter while seeing the patient, can note where dictation has been added or needs to be added. The database engine can then generate a large percentage of the note, adding in written, keyed or dictated (or whatever) information on the specifics. When the user indicates that something is to be added, the invention also indicates how the added dictation or note fits into the HCFA scheme. This then is a semi-automated rather than a completely automated format, because this is easier to use. It makes it easy for the user to "check off" standard items and to "add in" items unique to the individual encounter.

The assumption is that the note would be customized according to a physician's (or other health care workers) mode of practice or care delivery or according to the type of patient the physician or other health care worker was seeing.

As indicated above, the "form" goes through all of the items that are important for documenting compliance with HCFA regulations. The information entered is used to help determine and justify the billing level for the individual patient encounter. It provides all the information necessary for the computer to determine what the appropriate billing level might be and also provides the information needed to justify that level of billing. This is important because the new HCFA rules both are detailed and are complicated to apply accurately in a patient encounter setting. Because its simple design allows denoting findings quickly, it can be used when there are time pressures.

Take the case of a person being seen for the first time in an outpatient setting. The patient could be registered prior to being seen by a physician. This part of the registration process would include putting the patient's name, phone number, age, and other information into a database. This information would then be downloaded to the physician's portable device, desktop computer, or paper form, depending upon the practitioner's preference and need. The design of the pocket device is such that one can use the same pen both to write information on a piece of paper and to check off the answers to questions shown on the pocket device. The software includes history, physical, questions about medication, diagnostic options, medications, plans, and the like. It includes questions regarding the complexity of the problem that are important for medical billing purposes. The software leads the physician through all the elements of the examination and the physician checks off the appropriate items. The software includes history and "review of systems" questions, includes items related to the examination of the patient, and the like. The software allows the health care worker to indicate whether information has been added by dictation or writing, or will be typed later. The software provides a way for the health care worker to indicate what other activities were part of the encounter. (For example, looking at films or laboratory reports effect billing levels for physicians.) The results of the data entry can then be exchanged with the data base host. The data base host generates the clinic note and the letter and also generates the information regarding the intensity of service, which is needed for determining the billing level. The data base host is a figurative concept. In execution it could be either a single program, or several related programs. For example, the calculation of billing level could take place on the portable device, if this is used. It also could take place on a desktop computer or network server after the information is uploaded from the portable device. Notes generation could take place at the same time that billing level is calculated, or as part of a separate operation, depending upon the specific needs of the particular patient, encounter, or practice.

The discussion above emphasizes the use of this in documenting compliance with the HCFA/AMA documentation guidelines (DG). However, the intent of this invention is that compliance documentation be one of the results of use of the invention, but not the only use. The principle underlying this invention is that the proper focus of the health care worker's time should be on providing and documenting an encounter in the interest of patient care, not in the interests of reimbursement alone. The compliance documentation with respect to reimbursement is the result of the documentation, but not its sole focus. Instead, the idea behind this is to simplify the kinds of documentation, which physicians and other health care workers already are providing, make making these easier to read, organize and find. The ability to document compliance with DG is an outgrowth of this process, but not its central focus, from the perspective of the user.

In addition to obtaining a history, performing a physical, and deciding upon a course of action, the physician must convey the course of action to the patient. This is done in part by writing prescription, but also by discussing patients' problems and questions with patients and their families. In many cases, the physician may wish to provide written information that the patient can take home or may wish to document important elements of the conversation in the medical record. The invention allows the clinician to indicate, in a simple way, the items that have been discussed. The text engine can then summarize these discussions, and can select items of information that should be provided to the patient. These items can be developed ahead of time by the clinician, or could be purchased from others. The invention thus allows information to be documented for billing purposes, to be sent to other health care workers, and to be provided to the patient in a simple and straightforward manner. Depending upon the desires of the physician, the same information can be sent to everyone, or the information can be customized based upon the needs of the individual recipient. Similarly, the physician can identify prescriptions that should be sent to a pharmacy, and these can be sent automatically.

According to HCFA regulations, if "counseling" takes more than 50% of the time of the encounter, time alone can be the basis of the billing, if properly documented. The invention includes timing mechanisms to help determine if this is an appropriate basis for billing, and mechanisms for documenting the time and counseling appropriately.

In the setting of a teaching hospital, the HCFA documentation guidelines provide that an attending physician can utilize the documented observations of a resident. However DG also make clear that the attending must be explicit regarding what elements of the resident's history and physical are used and must note any changes. The invention facilitates this. If the resident has seen and documented a patient encounter using the invention, the results of this encounter can be reviewed by the attending in the same way. The resident's findings could be viewed and annotated by the attending on the same device or sheet, or transferred from one to the other.

The attending can indicate what features have been reviewed, what features have been personally examined by the attending, what differences there are in the attending's assessment as compared to the resident's assessment. This simplifies the documentation process and also assists in the training process, since messaging mechanisms can be utilized to explicitly indicate the differences to the resident. Communication could be through the database used by the institution or practice. One alternative would be that the resident would "send" the data to the database and the attending would then "get" this same data. If both resident and attending use appropriate handhelds, there could be direct infrared transfer between devices.

Whether or not the patient is seen in the setting of a teaching hospital, the invention facilitates referrals, since a referral note is but another type of note to be sent. The referral note can be generated from the entered data in much the same way as a chart note or letter is generated. The reason for the request can be "checked off" or written in a manner in keeping with the regulations.

The above gave the example of a portable device. Clearly, if this can be accomplished on a portable device, those skilled in the art can readily see that it can be accomplished on a desktop computer. More broadly, then, the method could be used on any system which included: a) a "user interface" (a method for the computer to present information to the user); b) a way of storing data and program instructions (such as a computer hard disc); and c) a means for the user to communicate with the computer (such as using a mouse, a pen input device, a keyboard, or voice dictation). The same also can be accomplished using scanner technology. In this case the "questionnaire" is on a piece of paper and the user would then use a pencil or pen to fill in the appropriate circles or squares. The paper would be scanned into a computer and the entered data would then be dealt with in a similar fashion.

The present invention is a tool that the provider can use directly, but the patient could use an embodiment of the invention as well. It however can receive information previously entered, be that information entered by the patient (as suggested by U.S. Pat. No. 4,130,881, mentioned above), or entered by another health care provider using the invention described here or another method of information entry. Going further, the spirit of the preferred embodiment is as follows. In most contemporary health care settings, there are existing standards and software that have been and are being used. The invention uses standard methods of obtaining, storing, and transmitting data. This facilitates integration of the invention into the broader setting of health care delivery within a given practice or institution. It also facilitates communication with third party payers, or with other institutions. For example, the database would be a standard commercial database, easily available to others, and the database storage would be such that a user familiar with database design and structure, or using standard tools, could easily examine its contents. The invention is compatible with UMLS (the Unified Medical Language System of the National Library of Medicine), The Arden Syntax for Medical Logic Modules (developed in part by ASTM, the American Society for Testing and Materials), SNOMED (Systematized Nomenclature of Human and Veterinary Medicine, College of American Pathologists), and other standard tools that integrate medical terms into a framework that allows them to be related to one another in a systematic and standardized way.

Although the embodiment described here refers specifically to the health care industry, those skilled in the art will envision that this method would be applicable to other industries that require a portable data entry device, detailed data entry, and calculations based on the entered data. Such adaptations and modifications are envisioned as being in the spirit of the invention and thus part of the invention.

BRIEF DESCRIPTION OF THE DRAWINGS

FIG. 1. The major elements of the Medical History and Physical as defined by the American Medical Association and Health Care and Financing Administration (available over the Internet at http://www.hcfa.gov/medicare/mcarpti.htm).

Figure 2:
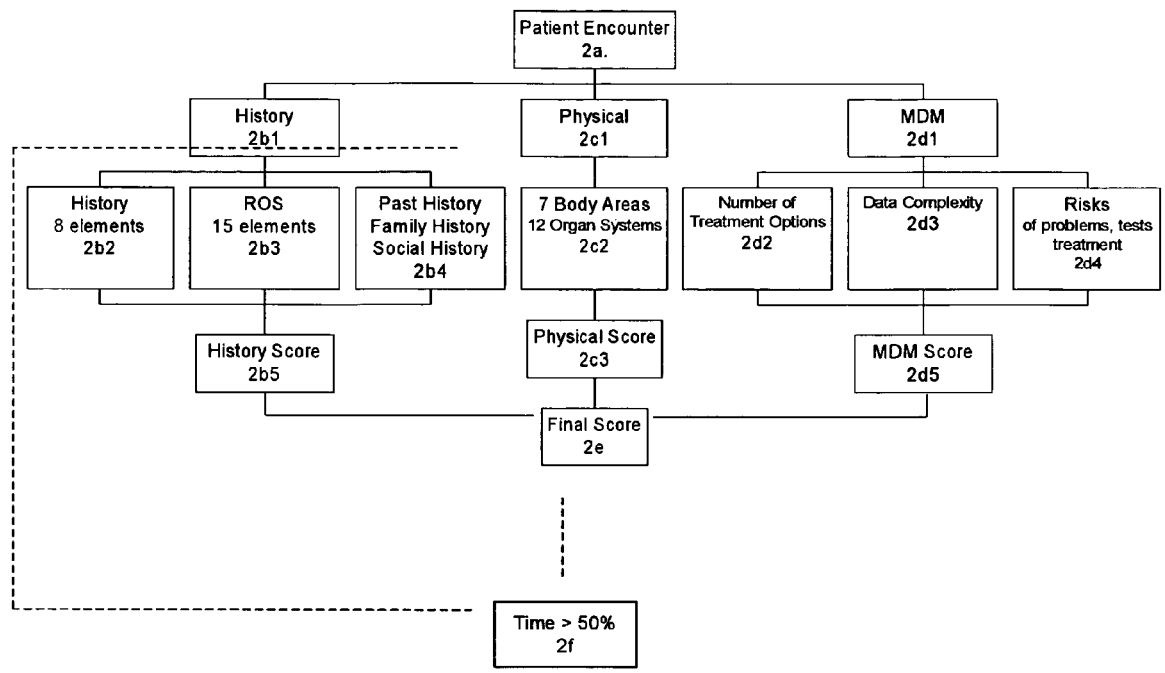
FIG. 2 and FIG. 3 outline the system design.

The drawings refer specifically to physicians, but the software presumes that similar guidelines will be developed for other health care workers, either by governmental agencies, or locally, because of Critical Path or other diagnosis and care initiatives.

DETAILED DESCRIPTION OF THE INVENTION

FIGS. 1a-1h summarize the elements of the medical evaluation as codified by the Health Care Financing Administration (HCFA) and American Medical Association (AMA). This document is titled "Documentation Guidelines for Evaluation and Management Services." This disclosure refers to this as DG.

The overall concept is to divide the process of evaluation and diagnosis into a number of elements. The HCFA/AMA system attempts to score all of the elements reflected in the record of a particular assessment. Based upon all of the sub-scores (derived from the individual elements of the examination) the system then requires the practitioner to come up with an overall "score" which reflects the level of effort and which itself is the code which will lead to billing and reimbursement. As will be seen, the scheme is complex. Figures summarizing this scheme are included because it is important to have an understanding of the intricacies of the scheme if one is to understand the role of the invention in simplifying application of the scheme.

The history is divided into the history of present illness per se, the review of systems, and the past, family and social history. The physical examination can comprise one or more of 7 body areas or 12 organ systems. Complexity of medical decision making pertains to the number of options available, the risks to the patient of the illness, diagnostic procedure, or treatment, and the type, amount, and complexity of data which need to be evaluated during the encounter.

FIG. 1a indicates that the three elements, as defined by DG, are history, physical examination, and medical decision making. The three major elements are further subdivided. FIG. 1b focuses on the defined elements of the history. In particular, 8 elements of the history of present illness have been defined. The practitioner is expected to make clear which element(s) of the history are reflected within each part of the chart note. There then is scoring, based on the number of elements documented in the note. For example, if the note indicates the duration of a problem, the context in which it occurs, and factors which modify it, there would be three elements within the history, and it would be defined as a brief history. However, if the problem were a chronic problem, it would be considered an extended history.

FIG. 1c shows the defined elements of the review of systems. There are 12 body systems defined by DG. Once again there is a scoring system, based upon the number of systems which are documented in the medical record.

FIG. 1*d* shows the past, family, and social history scoring system. There are no specific elements defined at this time for any of these three. The scoring is based upon how many of the three are reviewed in the record. For many physicians, the order in the regulations is different from the one traditionally used for notes. For example, the review of systems often comes after the past history. DG indicates that, in the actual note, the elements need not be in the order used in the regulations. However, physicians may be tempted to do it in this way, to make it easier for chart reviewers, who are not necessarily physicians, and who may or may not have previous health profession backgrounds. The invention would allow information to be entered in one order and then extracted in that order or others:. the needs of patient care and of patient billing may be different.

FIG. 1*e* shows how the "sub-scores" shown in FIGS. 1*b*-1*d* are put together to form an overall score for the history. In order to achieve a given scoring level, each of the three parts of the history must be at least at the level stated, but it is permissible for the "score" to be higher than the stated level. In other words, a detailed history must contain at least an extended history of present illness, at least an extended review of systems, and at least a pertinent past, family, and social history.

FIGS. 1*a*-1*j* summarizes the scoring system for the physical examination. DG distinguishes between specialty system examinations and what is called the general multi-system examination. Nine specialty examinations are defined. For illustrative purposes, FIGS. 1*g* and 1*h* indicate one such specialty examination, the neurological examination. It can be seen that certain of sections have bullets (for example, in the cardiovascular section, auscultation of heart, and others have small dots, but not bullets (for example, in the cardiovascular section, examination of carotid arteries. There is no clear distinction between these two in DG and the two presumably should be considered identical. In addition, some of the sections have heavier double lines, called "shading" by the HCFA/AMA (for example the Eye section). One reason for the confusion with respect to bullets, shading, and the like is probably that the file downloaded from the HCFA web site is displayed differently by different programs. What is a double line in the software (Microsoft Word) used to produce this document may be shading when viewed by other software (WordPerfect, for example).

In any case, FIG. 1*f* shows the scoring for the physical examination. Once again, there are several levels of examination, depending upon the number of systems of specified types that are assessed. For example, a detailed examination must include 12 bulleted elements, a comprehensive examination all bulleted, all shaded, and one unshaded element. The scoring for the physical examination varies among the various examination types (general multisystem examination and the nine specialty examinations; FIG. 1*f*/1 illustrates this schematically). The physician is expected to know the distinctions and perform the correct examination for the correct type of patient. A specialist, who might only learn one examination, could learn this, but it is more difficult for a primary care doctor, who sees many different kinds of patients, to accomplish this. It also presents difficulties for residents who rotate among services as a part of their medical training and who need to learn clinical medicine, let alone the intricacies of the DG system. The invention takes care of this for the physician. After the physician indicates what has been tested, and what kind of patient encounter is occurring, the invention determines the proper coding for this encounter, based upon the rules in the DG. The algorithm within the invention is flexible and can be easily modified to accommodate changes in the rules of the DG, or different rules from other third party agencies, such as insurance companies. The invention also can educate. For example, it can indicate what elements are needed for a given level of billing within a given type of examination.

FIG. 1*i* reviews the elements of what DG calls medical decision making (MDM). This portion of the scoring system divides into three subgroups. The first group within MDM, called the "number of diagnoses or treatment options," pertains to the kind of problem the patient has. For example, the problem can be self-limited, can be a problem known to the clinician, can be stable or can be worsening. The second group relates to the "amount or complexity of data to be reviewed." For example, does the clinician have to review laboratory tests, radiological studies? Does the clinician have to review old records or personally view images, traces of laboratory specimens? The third group seeks to summarize the "risks" to the patient of the disease, diagnostic tests, or treatments. DG provides suggestions regarding how to code for each of these groups and there is a table to help in coding risk (FIG. 1*j* reproduces this from DG).

It is important to note that this table gives representative examples but does not cover all situations. To give another example, the instructions for the first MDM group (not shown; this is a component of 1*i*) includes a category for an established problem which is stable or improved and one for an established problem that is worsening. However, "stable or improved" implies that things are going relatively well. What if a problem is bad, and remains bad? What is the appropriate category? There are additional examples throughout the DG. The invention allows clinicians to customize this table to match their practices and patient populations. Clinicians, practices, or institutions then could, for example, inquire to HCFA regarding specifics of their coding, and easily change the coding rules to accommodate HCFA rulings. Similarly, if the rules change, the algorithm can change the coding, and resultant billing, which occurs, either for future patient encounters, or retroactively.

The clinician is then expected to take the scoring from each of the sections just described and derive an overall score for the encounter with the patient. There are different rules for each of the 15 types of encounters defined by DG (for new hospital patient, new outpatient, established patient, consultation, etc.). In some cases there are three final levels of service to be scored, in other cases five. The rules for scoring the encounter for various service levels vary among the types of encounters, so that a given level of history, of examination, or of MDM could be scored differently for each of type of encounters. It can be seen the scoring system itself is complex, and it is clear that an inadvertent error might be made because of this complexity. On the other hand, the rationale behind the system is reasonable. It is that different kinds of effort take different amounts of time and intellectual effort and therefore should be compensated differently.

The rationale for this aspect of the invention is the following. The scoring system is complex, but it can be reduced to an algorithm. The algorithm is too complex for clinicians to calculate levels reliably in the course of a busy practice. Clinicians can be expected, however, to know what they actually do. Develop a simple means to allow them to document what they are doing when they do it. Allow them to use a simple check list format which will interfere as little as possible with clinical care. Make this microprocessor based so that the check list responses "fill in the blanks" of a database. Develop an algorithm that checks responses in the database and uses these to "score" the patient encounter. The microprocessor then can calculate the billing level based upon the algorithm. This would simply documentation, assure greater accuracy, increase consistency among physicians and over time, and facilitate chart reviews. It would allow the physician to concentrate on medical practice, and allow the billing and billing documentation to be an outgrowth of the documentation of the patient encounter, rather than its central organizing principle. As an additional benefit, the checked off items can be used to prepare at least a portion of the physician's note automatically, saving the physician's time.

The example given is of a physician, because of the DG. However, the same principles apply to notes prepared by nurses and other health professionals. Not all, but a large portion of a health care worker's documentation can be systematized, so that documentation can be prepared automatically. Going further, the principles described here can be applied to other industries where 1) data are acquired on the basis of an interaction between two or more people; 2) it is advantageous for data acquisition to be as unobtrusive as possible; 3) analysis of the acquired data is then expected; and 4) correspondence and other documentation are derived from this data.

FIG. 2 outlines the basic system design. There is a patient encounter (2a) and it is of a particular type, such as: New Patient, Office; Initial Hospital; Initial Inpatient Consult. There are 15 possible encounter types currently. The health care worker indicates this at the time of the encounter. Alternatively, in the case of a scheduled encounter, such as an outpatient visit, or prior to rounds on inpatients, the patient name, hospital registration number and other demographics, and the type of encounter, could be entered into the database "form" ahead of time. A history is obtained (2b 1) including the 8 elements of the "history of present illness, " the 15 elements of the review of systems (2b3), and the past, family, and social history (2b4). A physical examination (2c1) is performed and this can include any of 7 body areas or 12 organ systems (2c2). Medical Decision Making (MDM) (2d1) is composed of three subunits, the first related to number of treatment options (2d2), the second to data complexity (2d3), the third to risks of the medical problem, the diagnostic procedure, or the treatment (2d4).

A score (2b5, 2c3, 2d5) is derived from each of these three sections (2b, 2c, 2d). A final score is derived from 2b5, 2c3, 2d5. There are 64 possible combinations for each of the 15 types, for a total of 960 combinations. The rules for billing differ among these categories. The invention contains category specific algorithms to determine the appropriate billing level for the service provided. In some cases (new hospital in-patient, for example), there are minimum service levels that must be met before billing is allowable. The algorithm determines whether these minimum levels of service have occurred. In these cases, lower levels of service are not allowed during, for example, a hospital admission; higher levels of service are required. The invention would inform the physician when the information provided by that physician is not sufficient to justify billing. Similar scales have been constructed for the history, examination, and MDM sections.

Alternatively, billing can occur solely based on time (2f), if counseling of the patient takes over 50% of the time of the patient encounter. There are separate rules for this. The invention includes multiple timers to allow appropriate determination of the time of the visit, and of the counseling activities. It also facilitates documentation of the counseling itself.

An important feature of this invention is that all of the data entry elements, and all of the data output elements, can be customized by clinicians to meet the specifics of their practices. Data entry elements can be added to the sections for the history, physical, and medical decision making. These added elements can be linked in to the billing schema. Standard sections of output text can be defined and can be modified as needed for chart notes and correspondence. For example, there may be specific counseling that is performed routinely for a specific type of patient. The gist of the counseling could be summarized as a standard output text element that then could be included easily in the note.

Figure 3:
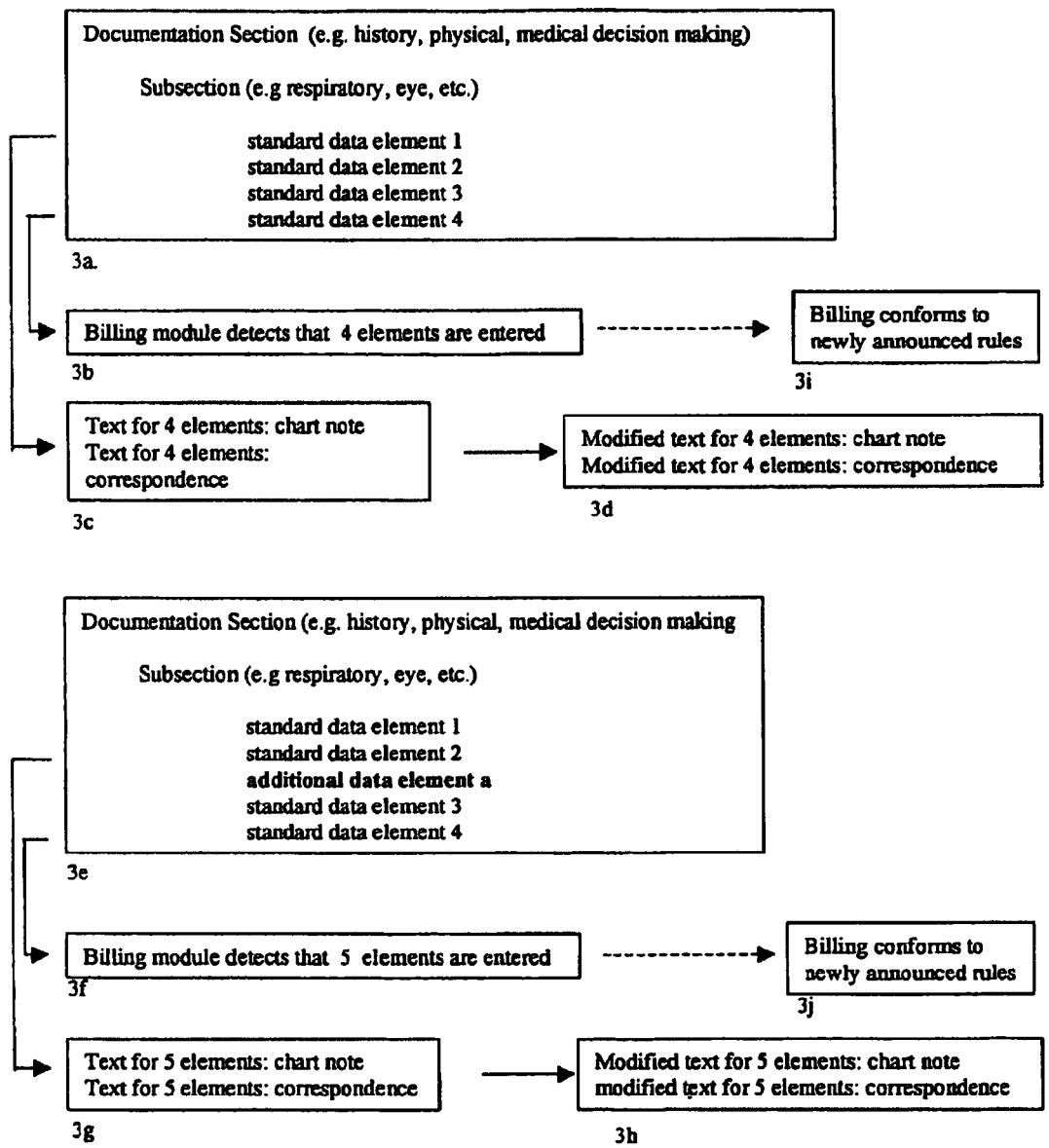

This is illustrated in FIG. 3. The invention as delivered to the user would contain default data elements to facilitate entry of information regarding the history, physical examination, and medical decision making (3a). It would also contain default billing algorithms (3b), and default text for correspondence (3c). The user can add elements to any section (an example is shown in 3e) and can define text output for these new elements (3g). The algorithm automatically adjusts for the presence of the new element (3f). In the example, there were four elements available and entered initially during a hypothetical encounter, one was added to the template. The user added an element (data element a, FIG. 3e). The user actually used all 5 of the elements now available when seeing a patient. The billing module detected this and scored accordingly (3f). Text output was automatically created for the five elements.

In addition, for both the original four and for the new group of five elements, the text output can be modified according to clinical needs or physician preference (3d, 3h). If the billing rules change, the coding can be changed to meet the new DG. The results of these changes can be applied either prospectively or retroactively. Retroactive changes can be for all previously entered data, or for only a subset, to conform to third party requirements (3I, 3j).

The physician enters the basic information for these sections. When appropriate, the system can ask relevant questions that help the algorithm to determine which elements to score. For example, the algorithm could ask (FIG. 2, 2d3) whether the physician is indicating what an x-ray report described or is describing the x-ray based on personal review. Such distinctions are important for billing purposes when using the DG schema. To give another example, the physician must state which type of examination was utilized (general multisystem, eye, dermatology, etc.). The system then scores the examination according to the requirements of the type of examination employed.

Figure 4A:
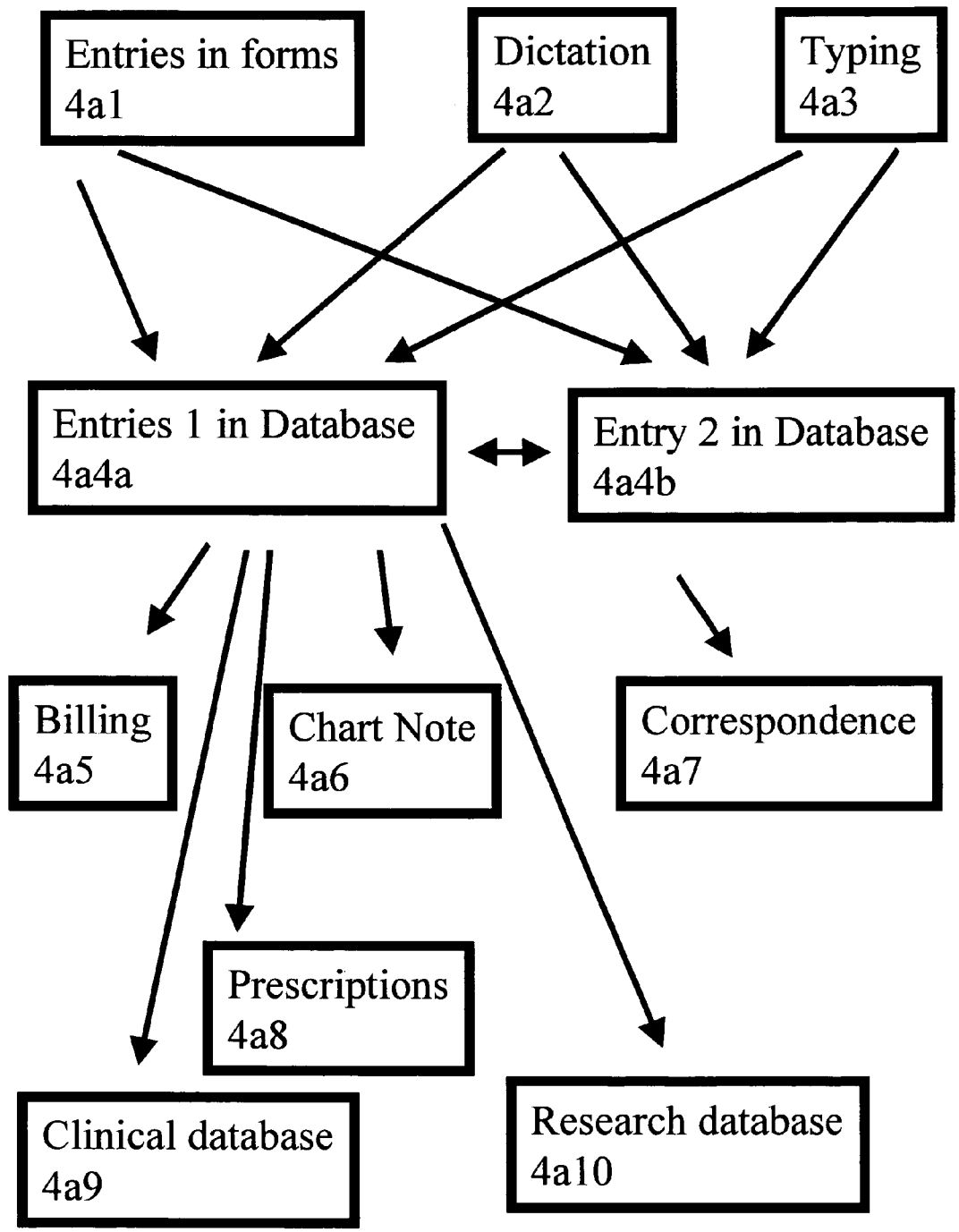
FIG. 4 indicates the flow of information as embodied in the invention.
Figure 5H:
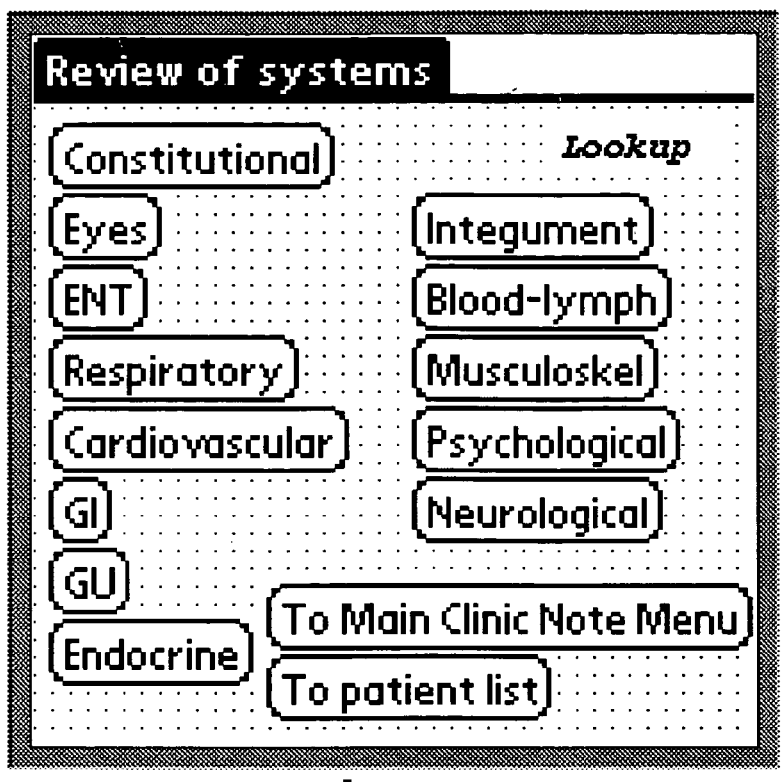
FIG. 5 demonstrates sample data entry screens from a preferred embodiment.

As FIG. 4a indicates, the method stores information in a database. Entries into the database can be made in many ways. For example, one could use a computer-based form (4a1), be the form actually on a computer, on a handheld device, or on paper, e.g. a form that can be scanned. In this case, the form would be designed with checklists, and the like. The design of the form would be "flat," without multiple layers of drag down or pop-up menus and submenus, to facilitate speed and ease of use. Data also could be dictated, "written," or keyed into the database. In the case of dictation (4b2), this could be traditional dictation, or computer based dictation using voice recognition. The same concepts apply to writing. Data could be "typed" into a form or as free text (4a3). In these cases, the system is designed to indicate where in the overall documentation the dictated or keyed information would go. The dictation or keyed input is then linked within the database (4a4) to the forms based input. Depending upon the needs of the situation, the user could dictate, write or key the name of the input screen and item, or there could be a unique identifier for each input screen or for each item on the screen. With computer based input, there could be automatic linking. That is, the user would highlight an item, or a screen, and the next input into the system (e.g. dictation, keyboard) would be linked to that highlighted position on the screen. The database scoring would then include that item for billing purposes. Assume, for example, that the user chose to dictate the details of palpation of the liver (see FIG. 5d.) The user would indicate the item (by highlighting it, for example, on a computer screen, or by checking off a box indicating an addition on a computer or paper form). The database would then "register" the dictated or keyed text at the appropriate point in the database.

More than one person might make entries regarding a particular medical encounter. For example, both the resident and the attending physician in a teaching hospital might prepare a note. In the case of a teaching hospital or a similar situation, the attending (e.g. 4a4b) could review the entries of the resident (e.g. 4a4a), make changes as may be appropriate, indicate items personally assessed, and indicate that the data has been reviewed and corrected. This permits explicit documentation of the nature of the attending's review of the resident's data entry, and also facilitates teaching, since the attending's edits of the resident's data entries could be "messaged" back to the resident. A similar mechanism could be used in the case of consultations. The consultant (4a4b) could explicitly review the requesting physician's note (4a4a). Where appropriate, a portion of the consultation report to the requesting physician could then explicitly be prepared in the context of the requesting note.

The database then uses the entered data to prepare, and justify, billing (4a5). The method uses the database entries to prepare chart notes (4a6) and other correspondence (4a7) and to prepare prescriptions (4a8). The entries in the database can be used to place entries into other clinical (4a9) or research (4a10) databases.

A feature of the data base design is the following. The documentation guidelines may change, or there may be a reinterpretation of the DG HCFA with a request that billing be recalculated based upon this new DG. In this circumstance, original records would have to be obtained and recoded given current methods. With the method outlined, recoding usually can occur in a simple manner by means of a simple change in the database tables followed by a structured query of the database.

The database is designed so as to provide several types of output. As already described, it codes for the level of service so as to satisfy DG for billing. It also generates chart notes and correspondence. It can do this using standard templates built in to the system. For example, (FIG. 5b) a check on an item in the review of systems can generate an appropriate comment in the note: check off arthritis and the note can say, "The patient has a history of arthritis." The physician can modify the templates according to personal preferences for documentation. All or a portion of the entered data can be used to populate a database used to monitor or facilitate clinical care, quality assurance, or research.

Figure 4B:
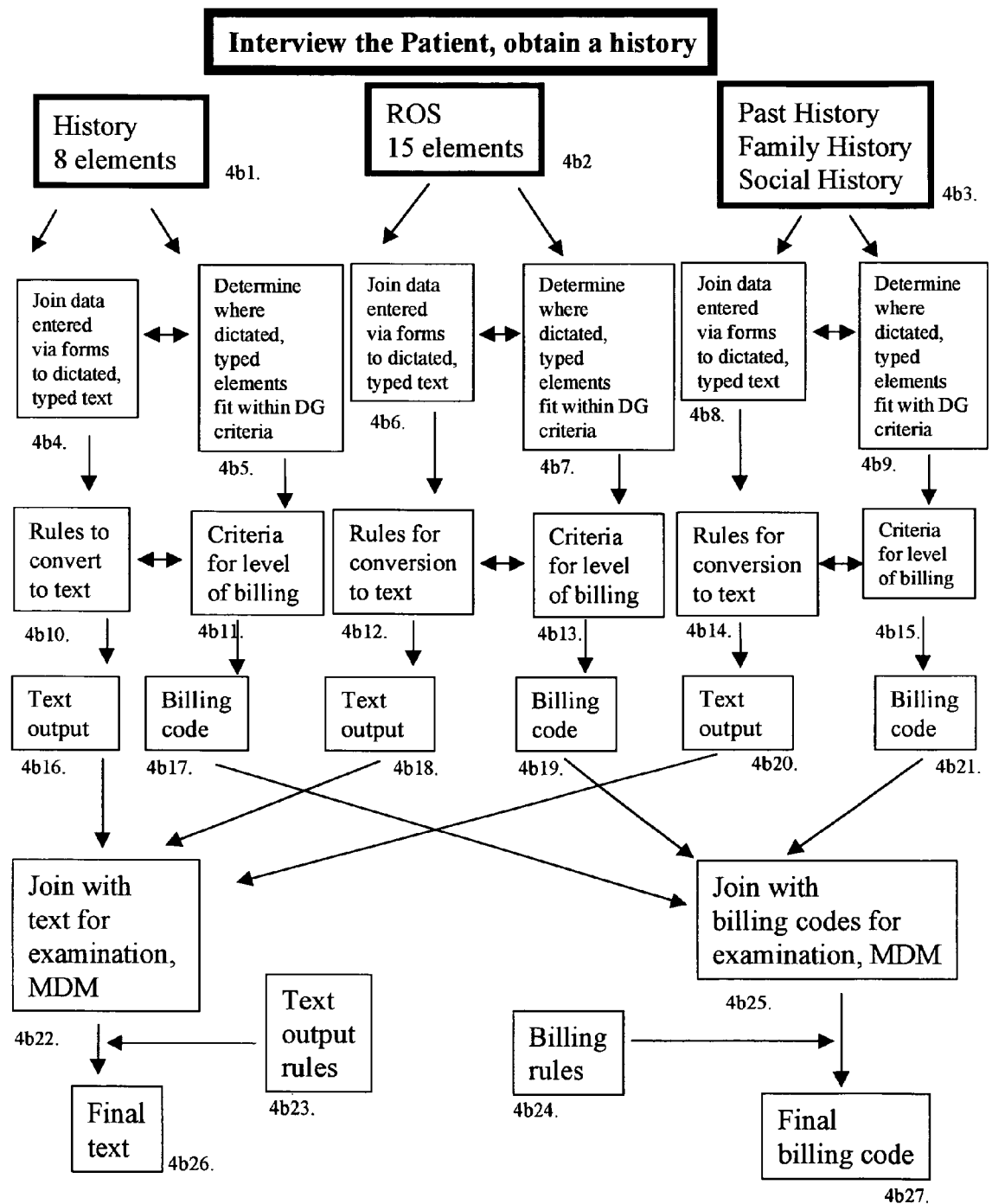

FIG. 4b illustrates the use of the database to provide both billing and text output. The example shows this for the elements of the history. The same principles apply to physical examination and medical decision making.

As FIG. 4b shows, and as reflected in the DG, there are three basic elements to the patient encounter: history, examination, and decision making process (4b1, 4b2, 4b3). The process employed by this invention is that the clinician enters data with regards to these three elements, entering the data either into a "form" (see FIG. 5 for an example) or by using free text (dictation, typing, etc.). The entered elements are joined together in the next stage. These can be joined to form a text note suitable for a medical chart, for dictation, etc. (4b4, 4b6, 4b8). The software also determines where the free text elements fit within the DG billing scheme (4b5, 4b7, 4b9). This is envisioned as a process wherein the user can indicate at the time of text entry where an element fits (e.g. by checking a box, see FIG. 5). Alternatively, the software can ask the user at the time that the clinician reviews the completed questions pertinent to the DG. The idea here is to make these questions part of the dictation review process, a process the clinician already knows. In the case of notes, correspondence and the like, there are rules within the method for how the combination of form based entries and free text entries are to be converted to a final text document (4b10, 4b12, 4b14). Where desired by the user, the invention can list the points that the clinician wishes or needs to include within the dictation. The method also assesses the combination of form and free text entries to determine the billing level (4b11, 4b13, 4b15). The rules for conversion to a text document result in text output for each of the three segments of the final note (4b16, 4b18, 4b20). These three are then joined together into the final document (4b22) together with addresses, salutations, signature sections, patient name and chart number, date, and other standard elements for the text. The method includes a way for the user to customize these elements, or add new elements. It also has rules for the appearance of the final text, again customizable for each type of text output (4b23). Embodied within 4b23 is the concept of educational materials which could be sent, for example, to a patient to help underline discussion points that occurred during the office visit. The physician thus can spend more time actually talking with the patient. There can be (previously prepared) items summarizing important points related to the discussion which has occurred. The physician can "check-off" the items which should be sent to the patient, to other health care providers, or to others, including insurers. Similarly, the method determines a code for each of the three elements of the patient encounter (4b17, 4b19, 4b21) and then determines the overall billing code (4b25), based upon the DG rules (4b24). The final text or texts (4b26) and final billing code or codes (4b27) are thus prepared.

An example of a table of values is shown in FIG. 4c, for initial hospital visits. The table is a codification of the Initial Hospital Care sections in Physicians' Current Procedural Terminology, Fourth Edition, CPT1998, published by the American Medical Association Column b row 2 shows 3/3, indicating that all three "scores" must be at the given level to justify a level of billing. Column c, row 1, shows the first four numbers of the billing code. The final number is listed below in the table as follows. The three elements, as noted above are A (history), B (Examination), and C (MDM). As described above, for history and for the examination there are four levels of effort (1-problem focused; 2-expanded problem focused; 3-detailed; 4-comprehensive). For MDM there similarly are four levels (1-straightforward; 2-low complexity; 3-moderate complexity; 4-high complexity). The numbers 3 3 1, 1, and 30 in column d indicate that the minimum value for a final score of 99221, A must equal at least 3, B equal at least 3, and C equal at least 1. The table then looks at all possible combinations of A, B, and C and lists what the final code would be. It indicates the combinations (denoted by n in the example) for which services can't be billed. The method is so constructed to allow changes in the codes as changes in DM occur. Simply changing the values, scale, or table could accommodate a different schema, for example from an insurance company. An alternative way of determining the proper level of billing would be by the use of decision trees. Using this alternative, the algorithm at each point would ask whether the encounter has included a particular activity or set of activities. If yes, the algorithm branches in one direction, if no, in the other. Those skilled in the art will recognize that branching algorithms of this type, although explicit, can be difficult to maintain, since a small change in the DG could require changes throughout the algorithm. A lookup table, such as used in this invention, is a simpler way for codifying the requirements of the DG and is simpler to maintain, and to check for errors.

The methodology helps to reduce duplication of effort on the part of the clinician. Typically, when clinicians wish to follow the care of a population of patients, the data regarding these patients must be entered separately from, and generally after, the clinical note is dictated or written. The problem is that in the course of a busy clinical practice, clinicians are pressed for the time to enter the data the second time (for the database). Moreover, even with the best of intentions, data entered later is likely to be less accurate than data entered at the time of the patient encounter. Data entry personnel can be hired, but this increases the expense of care.

Figure 5I:
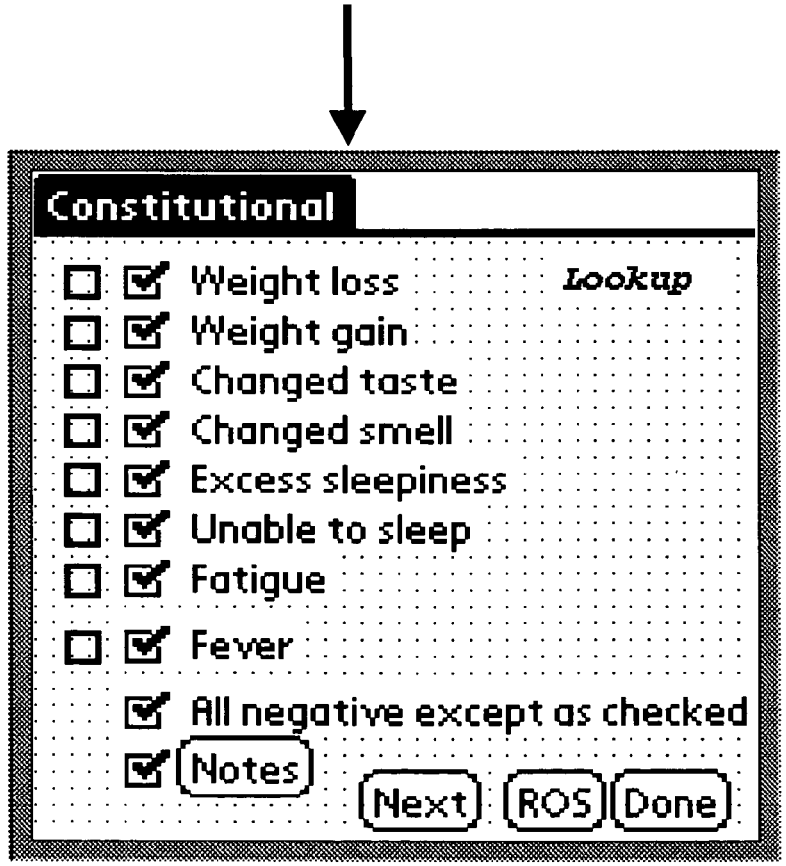

FIG. 5 demonstrates sample data entry screens from a preferred embodiment. This embodiment was developed for a handheld computer, the PalmPilot, but a similar methodology is asserted for other handheld computers, for desktop computers and for paper formats. FIGS. 5a and 5b depict sample screens from a review of systems (ROS). FIG. 5a lists questions for reviewing what are called constitutional symptoms, 5b, musculoskeletal symptoms. A check is placed in a box to indicate the presence of a symptom. If only one or two are present, and the rest are not, the clinician can indicate this in a simple way, without having to enter a check on each line. Alternatively (if desired) there could be two boxes, one to indicate that a symptoms is present, and another to indicate that it is not. (See FIG. 5i.) The "all negative except as checked" could still be used. At the bottom left are a check box and the word "Notes." The check box is meant to indicate the concept, noted above, of indicating an addition to the form at the appropriate point in the form. The check would indicate that there was text to insert at this point. Alternatively, the word "note" is a button on the computer form. "Pushing" the button would take the user to a blank page where free text information could be entered directly. By highlighting an item and then pressing the note button, for example, the user indicates to the system that a note is to be added to that item. That added note could be highlighted, if desired, at the time the note is reviewed. In a similar way, if a resident or other caregiver has seen the patient before the attending, check boxes can be used so that the attending can indicate review of the previously entered information.

FIGS. 5c and 5d show representative screens for the Constitutional examination and the Abdominal examination. The explanations in the previous paragraph again apply. There also are fill-in sections for blood pressure, pulse, and the like, or these could have been entered previously.

For FIGS. 5a-d, there are buttons at the bottom labeled Prev, Next, ROS, Exam, and Done. Previous and Next take the user to the previous and next screens for that portion of the evaluation. Exam and ROS take the user to the main screen for physical examination and Review of Systems respectively. FIG. 5h gives an example of an ROS "main screen," listing all the possible systems to be reviewed. Pressing "Done" indicates that the user has completed that section of the evaluation (i.e. the ROS section). Note that there are relatively few items on a given "page" and that all items are accessible without going into more than a single submenu or subform.

FIG. 5e shows a checklist for treatment plans for a patient. This particular set of forms was designed for use in an epilepsy clinic, so that the medications are anticonvulsants. The same principals would apply to any clinical setting, however. The user employs a check to indicate what the treatment plan is for the patient. If the physician has a standard way in which the medication is to be used, the check can generate, via the database, chart notes, correspondence, prescriptions, and patient educational materials indicating how the medication is to be used. FIG. 5f shows a form for use in indicating drug doses. FIG. 5g indicates various treatment options for patients who are candidates for surgical treatment for their seizures.

In these examples, a standard protocol could be developed by, and be used by, the clinician. In such a case the check is sufficient to "trigger" the protocol. However, this is not required. As in the previous examples, the clinician could highlight an item and dictate additionally in regards to it. The clinician could prescribe the treatment in a "non-protocol" manner. A button or check box for notes also could be included.

There is a problem with current computerized patient records, as well as with computer software in general which uses what is commonly called a graphical user interface or GUI. This is that the user must navigate through a series of levels in order to get to a certain function or enter a certain type of information. The problem is that the clinician doesn't have the time to navigate down through layers of menus and submenus to find a given choice. This layering tends to discourage use of the form.

This complexity may in part have developed because of a wish that the form be as complete as possible. However, this completeness results in an increased complexity of use. Data entry formats must be simple to use. If they are not, people won't use them. The concept of the present invention is that a large percentage of the history and physical, perhaps 70% or more, lends itself to entry into simple data entry formats such as described here. The balance does not. This invention does not expect all to be entered by means of a form. Because it does not, the form is easier to use. Dictation, typing, or similar means can enter the balance. Data entered by form can be blended easily with data entered by dictation or typing using the methods described. As voice and handwriting recognition and similar techniques begin to be used, such information will be able to go immediately into the appropriate portion of the database.

The data entry for this invention is as "flat" as possible, with a maximum of one submenu on any data entry page. The rationale is that a physician tends to ask a set series of questions, and perform a set series of tests, regarding a given problem. The data entry format seeks to mirror this process. Rather than navigating "down" to a submenu, the user touches the "next" button to go to the next menu for that form. The user can arrange the order of the forms to conform to personal tastes and habits or to meet the needs of the patient encounter. As already noted, the same principles would apply to data entry by other health care workers, and by workers in other industries.

What is claimed is:

1. A method of calculating a billing code for a patient encounter that complies with the requirements of the United States Health Care Financing Administration (HCFA) (now known as Centers for Medicare and Medicaid Services (CMS)) (collectively HCFA/CMS), including the steps of:
    (a) providing an electronic computer or scannable form;
    (b) prompting a user via said electronic computer or scannable form to collect information regarding said patient encounter, said information including at least certain information relevant to calculating said billing code;
    (c) collecting and recording said information regarding said patient encounter using said electronic computer or said scannable form into a data base or data table; and (d) using said electronic computer or said scannable form to electronically derive an appropriate HCFA/CMS billing code from said collected information.

2. The method of claim 1, in which said electronic computer or scannable form is provided in the form of a handheld computer with a touch screen interface, and said recording step includes entering the information in real time into said electronic computer via said touch screen interface.

3. The method of claim 1 or claim 2, wherein said electronic computer is at least one of desktop computer, computer terminal, laptop computer, handheld computer, handheld device, voice recognition device, voice recognition software, and scannable forms.

4. The method of claim 1, wherein said billing code is based at least in part on comparing a total patient encounter time and a total patient counseling time.

5. The method of claim 1 further including storing patient counseling information and patient care information, and using said stored information for clinical care, prescriptions, counseling materials, educational materials, correspondence, quality assurance, billing, research, historical tracking and/or analyzing.

6. The method of claim 1, further including: computer-readable patient-administered information forms for obtaining certain data related to patient care or to Health Care Financing Administration (HCFA) (now known and Centers for Medicare and Medicaid Services (CMS)) (collectively HCFA/CMS) requirements.

7. Apparatus for compiling medical data and generating a billing code based on said medical data and being consistent with payer mandates, comprising:
    electronic means for displaying items for evaluation of a patient during a patient encounter, said items being at least sufficient to support billing requirements imposed by said payer mandates;
    data forms for collecting and storing patient responses and/or user findings regarding history, examination, assessment, counseling, or decision occurring as a result of said patient encounter;
    means for storing and accessing said patient responses and/or said user findings;
    an algorithm for linking and comparing said patient responses and/or said user findings with values for billing, procedure, treatment, counseling and/or documentation requirements; and
    calculating means for deriving a resultant code based in part on said algorithm.

8. The apparatus of claim 7, wherein said resultant code is an evaluation and management code to be used in a claim and for submitting to a payer.

9. The apparatus of claim 7, further comprising a timer for tracking total time and patient counseling time during said patient encounter, and algorithm for computing the percent of total time used for counseling.

10. The apparatus of claim 8, wherein said billing codes are Health Care Financing Administration (HCFA) (now known as Centers for Medicare and Medicaid Services (CMS)) (collectively HCFA/CMS) codes.

11. The apparatus of claim 7, wherein said billing codes are insurance requirement codes.

12. The apparatus of claim 8, 9, 10 or 11 wherein said electronic means comprising one of desktop computer, computer terminal, laptop computer, handheld computer, handheld device, voice recognition device, voice recognition software, handwriting recognition device, or hand writing recognition software.

13. The apparatus of claim 7, wherein said electronic means comprises at least one of desktop computer, computer terminal, laptop computer, handheld computer, handheld device, voice recognition device, voice recognition software, and scannable paper forms.

14. The apparatus of claim 7, wherein said billing code is based at least in part on comparing a total patient encounter time and a total patient counseling time, and determining said billing code based upon said comparison.

15. The apparatus of claim 7 or 8, wherein said data includes patient counseling information and patient care information.

16. The apparatus of claim 7, further including using said stored patient responses and/or user findings for clinical care, prescriptions, counseling materials, educational materials, correspondence, quality assurance, billing, research, historical tracking and/or analyzing.

17. An integrated electronic system for conducting a medical interview of a patient and contemporaneously compiling medical data and calculating an appropriate Evaluation and Management billing code based on that interview, including:
    electronic means including:
    a prompting means for generating real-time prompts to prompt an interviewer to make a series of inquiries for eliciting responses from the patient during a patient encounter, said series of inquiries and said responses including at least sufficient details to support billing requirements imposed by payer mandates, said series of inquiries including individual data elements needed to calculate or derive the Evaluation and Management billing code,
    said prompting means further including:
    a calculating means for calculating further prompting for inquiries regarding the patient using at least some of the preceding responses;
    a guiding means for guiding the interviewer during said interaction with the patient;
    a reminding means to remind the interviewer regarding specific points of inquiry relevant to further examination of that patient; and
    a soliciting means to solicit underlying information usable for calculating a description of the medical services being provided, said underlying information comprising details of a patient history, details of a patient examination and/or details of medical decision making regarding a patient diagnosis, details of medical tests to describe, diagnose and/or treat the patient, information used for clinical research, information used for quality assurance, and/or information used to compile patient care data base information;
    the electronic means further including:
    a recording means for recording said responses or other related information corresponding to the series of inquiries; and
    a calculating means using information including said recorded responses to derive the Evaluation and Management billing code, said billing code complying with the billing requirements imposed by said payer mandates.

18. The system of claim 17, wherein the billing code is based at least in part on comparing a total patient encounter time and a total patient counseling time.

19. The system of claim 17, where said billing code is based on billing requirements imposed by the United States Health Care Financing Administration (now known as Centers for Medicare and Medicaid Services (CMS)) codes.

20. The system of claim 17, in which said electronic means comprises a handheld computer with a touch screen interface, said interface facilitating the recording of information in real time.

21. The system of claim 17, wherein said electronic means comprising one of desktop computer, computer terminal, laptop computer, handheld computer, handheld device, voice recognition device, voice recognition software, handwriting recognition device, hand writing recognition software or scannable form.

22. An apparatus for assisting a user in conducting a patient encounter, said patient encounter comprising inquiry, examination, assessment, counseling, or decision regarding said patient, storing data regarding said patient encounter, and generating a billing code based on said patient encounter data, including:
  prompting means for reminding the user to enter individual data elements, wherein said data elements comprise data needed to indicate the type of patient encounter, to document what was found or what occurred during said patient encounter, and/or to comply with requirements for calculation of said billing code specific for said type of patient encounter;
  inputting means for recording said patient encounter data;
  data storage means for preserving said patient encounter data;
  calculating means for using said data regarding said patient encounter to derive for the user said billing code, said billing code complying with billing requirements imposed by payer mandates for said type of patient encounter; and
  data access means wherein items preserved by said data storage means and results of said calculating means can be viewed, analyzed, or revised.

23. A method for assisting a user in conducting a patient encounter, said patient encounter comprising inquiry, examination, assessment, counseling, or decision regarding said patient, storing data regarding said patient encounter, and generating a billing code based on said patient encounter data, including:
  providing the apparatus of claim 22; said method further including at least one of the following steps:
  the apparatus prompting the user to enter individual data elements, wherein said data elements comprise data needed to indicate the type of patient encounter, to document what was found or what occurred during said patient encounter, or to comply with requirements for calculation of said billing code specific for said type of patient encounter;
  the user inputting said patient encounter data;
  electronically storing said patient encounter data;
  calculating from said data regarding said patient encounter to derive for the user said billing code, said billing code complying with billing requirements imposed by payer mandates for said type of patient encounter; and
  accessing said data and/or said results of said calculating step for viewing, communicating, analyzing, or revising same.

24. The method of claim 23, wherein said billing code is derived based on rules set forth in the Documentation Guidelines for Evaluation and Management Services billing code of the Health Care Financing Administration (HCFA), now called Centers for Medicare & Medicaid Services (CMS).

25. The method of claim 23, said step of electronically storing said patient encounter data including storing patient counseling information and patient care information.

26. The method of claim 23 or claim 25, further including using said stored patient encounter data for clinical care, prescriptions, counseling materials, educational materials, correspondence, quality assurance, billing, research, historical tracking and/or analyzing.

27. The apparatus of claim 22, said data access means including means for preparing communications regarding results of said patient encounter and said calculating means, said communications including documentation regarding what was found or what occurred during said evaluation, documentation sufficient to support said billing code, and/or communications to other health care providers.

28. The apparatus of claim 22, said data access means including means for facilitating use of said information in connection with clinical research, quality control, patient care data base information, clinical notes, clinical counseling notes, or correspondence.

29. The apparatus of claim 22, wherein said calculating means comprises a timer for tracking total time of patient encounter and total counseling time during said patient encounter, and an algorithm for comparing said total time of said patient encounter and said total counseling time during said patient encounter, and determining whether said billing code should be based upon said comparison.

30. The apparatus of claim 22, wherein said electronic means comprises a personal computer, desktop computer, laptop computer, network server, handheld computing device, portable computing device, or scannable form.

31. The apparatus of claim 22, wherein said data storage means comprises a data base or data tables.

32. The apparatus of claim 31, wherein said data base or data tables are modifiable as needed.

33. The apparatus of claim 22, further comprising an adding means, wherein said user can add free text to said data elements, said free text entered by said user by means comprising voice dictation, voice recognition software, handwriting, or direct keyed entry.

34. The apparatus of claim 22, wherein said prompting means is customizable to accommodate needs of specific medical practices.

35. The apparatus of claim 22, wherein said prompting means is modifiable to accommodate changes in said payer mandates and clinical practice.

36. The apparatus of claim 22, wherein said prompting means is customizable to accommodate the needs of medical encounters, medical practices, or users.

37. The apparatus of claim 22, wherein said data access means is customizable according to needs of said medical encounter or of said user.

* * * * *

UNITED STATES PATENT AND TRADEMARK OFFICE
CERTIFICATE OF CORRECTION

| | |
|---|---|
| PATENT NO. | : 7,801,740 B1 |
| APPLICATION NO. | : 09/157998 |
| DATED | : September 21, 2010 |
| INVENTOR(S) | : Ronald Peter Lesser |

It is certified that error appears in the above-identified patent and that said Letters Patent is hereby corrected as shown below:

CROSS-REFERENCE TO RELATED APPLICATIONS
Column 1, line 9, "Not applicable" should read --This application claims priority to U.S. Provisional Application Serial No. 60/097,290, filed August 20, 1998, the content of which is incorporated herein by reference in its entirety.--

DETAILED DECRIPTION OF THE INVENTION
Column 9, line 27, "FIGs. 1a-1j summarizes" should be --FIG. 1f summarizes--
Column 15, line 54, "Prey" should be --Prev--

CLAIM 7
Column 17, line 38, "assessment, counseling or decision" should be --assessment, counseling and/or decision--

CLAIM 9
Column 17, line 54, before the word "algorithm" should be --an--

CLAIM 10
Column 17, line 56, "claim 8" should be --claim 7--
Column 17, line 56, "codes" should be --code--
Column 17, line 56, "are" should be --is a--
Column 17, line 59, "codes" should be --code--

CLAIM 12
Column 17, line 62, "claim 8, 9, 10 or 11" should be --claim 8 or claim 9--

CLAIM 19
Column 18, line 67, the word "codes" should be deleted

Signed and Sealed this
Eighteenth Day of January, 2011

David J. Kappos
*Director of the United States Patent and Trademark Office*

CERTIFICATE OF CORRECTION (continued)
U.S. Pat. No. 7,801,740 B1

CLAIM 22
Column 19, line 13, "or" should be --and/or--
Column 19, line 34, "or" should be --and/or--

CLAIM 23
Column 19, line 37, "or" should be --and/or--
Column 19, line 47, "or" should be --and/or--

CLAIM 24
Column 20, line 3, the words "billing code" should be deleted